United States Patent

Shibanuma et al.

[11] Patent Number: 6,080,900
[45] Date of Patent: Jun. 27, 2000

[54] PROCESS FOR FLUORINATING HALOGENATED HYDROCARBON

[75] Inventors: Takashi Shibanuma; Takashi Kanemura; Satoshi Koyama, all of Osaka, Japan

[73] Assignee: Daikin Industries Limited, Osaka, Japan

[21] Appl. No.: 08/116,550

[22] Filed: Sep. 7, 1993

Related U.S. Application Data

[63] Continuation of application No. 07/886,823, May 22, 1992, abandoned.

[30] Foreign Application Priority Data

May 23, 1991 [JP] Japan ................................. 3-118437

[51] Int. Cl.$^7$ .................................................. C07C 17/08
[52] U.S. Cl. ........................... 570/168; 570/166; 570/169
[58] Field of Search ................................... 570/168, 169, 570/186

[56] References Cited

U.S. PATENT DOCUMENTS

| | | |
|---|---|---|
| 2,745,886 | 5/1956 | Ruh et al. . |
| 2,885,427 | 5/1959 | Ruh et al. . |
| 3,426,008 | 2/1969 | Chapman et al. . |
| 3,644,545 | 2/1972 | Buckman . |
| 3,755,477 | 8/1973 | Firth et al. . |
| 4,158,675 | 6/1979 | Potter . |
| 4,311,863 | 1/1982 | Gumprecht . |
| 4,766,259 | 8/1988 | Manzer et al. . |
| 4,792,643 | 12/1988 | Sobolev . |
| 5,051,537 | 9/1991 | Manzer .................................. 570/168 |

FOREIGN PATENT DOCUMENTS

| | | |
|---|---|---|
| 0313991 | 9/1989 | European Pat. Off. . |
| 0366797 | 5/1990 | European Pat. Off. . |
| 1252182 | 10/1967 | Germany . |
| 3910310 | 6/1939 | Japan . |
| 423004 | 2/1942 | Japan . |
| 49-43922 | 11/1974 | Japan . |
| 51-54503 | 5/1976 | Japan . |
| 51-82206 | 7/1976 | Japan . |
| 52-33604 | 8/1977 | Japan . |
| 57-132549 | 8/1982 | Japan . |
| 60-19038 | 1/1985 | Japan . |
| 62-186945 | 8/1987 | Japan . |
| 62-44973 | 9/1987 | Japan . |
| 17413 | 3/1989 | Japan . |
| 1221338 | 9/1989 | Japan . |
| 1228925 | 9/1989 | Japan . |
| 1268651 | 10/1989 | Japan . |
| 1272535 | 10/1989 | Japan . |
| 295438 | 4/1990 | Japan . |
| 2172933 | 7/1990 | Japan . |
| 2030981 | 4/1980 | United Kingdom ................... 570/168 |
| 2030981 | 4/1990 | United Kingdom . |
| 8910341 | 11/1989 | WIPO . |

*Primary Examiner*—Alan Siegel
*Attorney, Agent, or Firm*—Birch, Stewart, Kolasch, & Birch, LLP

[57] ABSTRACT

A halogenated hydrocarbon is effectively fluorinated by reacting the halogenated hydrocarbon with hydrogen fluoride in the presence of a fluorination catalyst which comprises a partially fluorinated chromium oxide containing at least one metal selected from the group consisting of ruthenium and platinum.

9 Claims, No Drawings

PROCESS FOR FLUORINATING HALOGENATED HYDROCARBON

This application is a continuation, of application Ser. No. 07/886,823 filed on May 22, 1992, now abandoned.

BACKGROUND OF THE INVENTION

1. Field of the Invention

The present invention relates to a process for fluorinating a halogenated hydrocarbon. More particularly, the present invention relates to a process for preparing a hydrocarbon such as 1,1,1,2-tetrafluoroethane which is useful as a refrigerant, a blowing agent, a propellant, a cleaning agent and the like.

2. Description of the Related Art

As a fluorination catalyst, chromium oxide which may be supported on alumina is known (see Japanese Patent Publication Nos. 10310/1964, 3004/1967 and 44973/1987 and U.S. Pat. Nos. 3,426,009, 3,755,477 and 4,158,675). Also, fluorination in the presence of a chromium salt or partially fluorinated chromium oxide which may be supported on a carrier is known (see U.S. Pat. Nos. 2,745,886 and 2,885,427, DE Patent No. 1 252 182, Japanese Patent Publication No. 54503/1976, Japanese Patent Kokai Publication No. 132549/1978 and WO89/10341).

There is also known a catalyst comprising chromium oxide and an additive such as NaF (U.S. Pat. No. 3,644,545), Mg or Ba (Japanese Patent Publication No. 43922/1974), a transition metal (U.S. Pat. No. 4,792,643) or AlPO$_4$ (Japanese Patent Publication No. 17413/1989). Further, there are known processes using a catalyst comprising metal chromium (Japanese Patent Kokai Publication Nos. 19038/1985 and 221338/1989) or a metal other than chromium (Japanese Patent Kokai Publication Nos. 186945/1987, 268651/1989, 172933/1990 and 95438/1990).

U.S. Pat. No. 4,766,259 discloses a fluorination reaction using partially fluorinated aluminum oxide.

A liquid phase fluorination reaction using a Sb catalyst is known. In addition, a liquid phase fluorination reaction using an alkali metal fluoride as a catalyst is known (see U.S. Pat. No. 4,311,863 and Japanese Patent Kokai Publication No. 228925/1989).

Now, the fluorination of a halogenated hydrocarbon is explained by making reference to the preparation of 1,1,1,2-tetrafluoroethane (hereinafter referred to as "134a") through fluorination of trichloroethylene or 1,1,1-trifluorochloroethane (hereinafter referred to as "133a") in a gas phase. It is not advantageous to synthesize 134a from 133a by a liquid phase reaction in view of a low yield and a material of a reactor.

When the above fluorination reaction is carried out in a gas phase, conversion of 133a to 134a is low due to equilibrium. Therefore, a catalyst to be used should catalyze this reaction at a relatively low conversion and have a sufficiently long life and a good selectivity in an industrial use. Prolongation of the catalyst life avoids frequent change of the catalyst and lowers the catalyst cost.

The catalyst life can be prolonged by the addition of chlorine gas (Japanese Patent Publication No. 33604/1977) or oxygen gas (GB Patent No. 2 030 981 and Japanese Patent Kokai Publication Nos. 82206/1976 and 272535/1989) to a reaction gas mixture. When the chlorine gas is added, selection of a material of a reactor may be limited and also increase in by-products will be considered. When the oxygen gas is added, a conversion may be decreased.

In view of the above, it is advantageous to provide a catalyst which has a long life as such. When such catalyst is excellent in catalytic activity, not only is the catalyst cost, but also the size of a reactor which is made of an high quality expensive material can be reduced advantageously.

SUMMARY OF THE INVENTION

One object of the present invention is to provide an improved catalyst which can catalyze a gas phase fluorination of a halogenated hydrocarbon.

Another object of the present invention is to provide an improved process for fluorinating a halogenated hydrocarbon in a gas phase.

According to the present invention, there is provided a process for fluorinating a halogenated hydrocarbon comprising reacting a halogenated hydrocarbon with hydrogen fluoride in the presence of a fluorination catalyst which comprises a partially fluorinated chromium oxide (III) containing at least one metal selected from the group consisting of ruthenium and platinum. In particular, the present invention provides a process for preparing 134a by reacting 133a with hydrogen fluoride in the presence of the above catalyst according to a reaction formula:

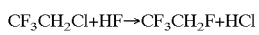

$$CF_3CH_2Cl + HF \rightarrow CF_3CH_2F + HCl$$

DETAILED DESCRIPTION OF THE INVENTION

Herein, the term "halogenated hydrocarbon" intends to mean a hydrocarbon having at least one halogen atom other than fluorine atom.

Examples of the halogenated hydrocarbon to be fluorinated by the process of the present invention are 133a, $CCl_4$, $CHCl_3$, $CH_2Cl_2$, $CH_3Cl$, $CCl_3F$, $CCl_2F_2$, $C_2Cl_4$, $C_2Cl_3H$, $CHCl_2CF_3$, $CHClFCF_3$, etc.

The catalyst used according to the present invention comprises chromium oxide or chromium hydroxide carrying at least one metal selected from the group consisting of ruthenium and platinum. Chromium oxide or chromium hydroxide may be supported on a carrier such as aluminum oxide, fluorinated aluminum oxide or aluminum fluoride. A content of ruthenium or platinum is from 0.01 to 10% by mole, preferably from 0.01 to 6% by mole based on an amount of chromium oxide or chromium hydroxide. When the content of ruthenium or platinum is too large, the catalytic activity may be deteriorated.

To carry ruthenium and/or platinum on the catalyst, their chloride, hydroxide, oxide, chlorometallic acid, and the like are used.

Ruthenium and/or platinum can be carried on the catalyst by impregnation, precipitation or mixing.

When chromium hydroxide is used, chromium hydroxide carrying ruthenium and/or platinum is sintered to convert chromium hydroxide to chromium oxide and fluorinated with hydrogen fluoride. When chromium oxide is used, it is fluorinated after ruthenium and/or platinum are added. While ruthenium or platinum is present in a metal form, its surface is partially covered with a fluoride. Chromium oxide is partially fluorinated. The term "partially fluorinated" intends to mean that chromium oxide contains 8 to 48% by weight, preferably 15 to 44% by weight of fluorine.

In the reaction according to the present invention, the conversion and/or the catalyst life can be adjusted by changing reaction conditions such as a molar ratio of hydrogen fluoride to the halogenated hydrocarbon, a reaction temperature, etc. When 133a is fluorinated, a molar ratio of hydrogen fluoride to the halogenated hydrocarbon is from 0.9:1 to 16:1, preferably 1:1 to 10:1, and the reaction temperature is from 290° C. to 380° C.

A reaction pressure is not critical. However, a pressure higher than atmospheric pressure is not preferable since the catalytic activity is reduced.

PREFERRED EMBODIMENTS OF THE INVENTION

The present invention will be explained further in detail by following Examples.

In Examples and Comparative Examples, common reaction conditions were employed. That is, a molar ratio of hydrogen fluoride to a raw material 1,1,1-trifluorodichloroethane was 1:1, a reaction temperature was 350° C., and a contact time (namely a ratio (g.sec/Nml) of a catalyst weight W to a flow rate F) was 0.4. The maximum conversion achieved by these conditions was about 13% (equilibrium conversion).

A reactor was a Hasteloy C made tube having an inner diameter of 15 mm, and a gas flow rate was 600 ml/min.

The definitions of an activity, a catalyst life and a throughput are as follows:

The activity is the achieved maximum conversion (%).

The catalyst life is a time (hr) at which the conversion decreased to 60% of the maximum value.

The throughput is an amount of the reaction product (134a) produced by one gram of the catalyst till the catalyst life time.

Preparation of Standard Catalyst

A partially fluorinated chromium oxide catalyst which contains no additional metal and is used as a standard catalyst was produced as follows:

To a 5.7% aqueous solution of chromium nitrate, 10% aqueous ammonia in an equivalent amount was dropwise added to precipitate chromium hydroxide. The precipitate was filtered, washed with water and dried in an air at 120° C. for 12 hours. The catalyst at this stage is referred to as "chromium hydroxide state catalyst"

This catalyst was pelletized by a pelletizer and kept in a nitrogen stream at 400° C. for 2 hours (sintering), followed by fluorination with hydrogen fluoride (HF treatment). Then, the catalyst was ground to powder having a particle size of 300 to 1000 micrometers. Four grams of the ground catalyst was used in the reaction. This catalyst was used as a standard catalyst.

COMPARATIVE EXAMPLE 1

Using a standard catalyst produced from the same chromium hydroxide state catalyst as used in Example 1, the fluorination was carried out under the above common conditions. The results are as follows:

Activity: 12.6%

Catalyst life: 78 hours

Throughput: 177 g

EXAMPLE 1

The chromium hydroxide state catalyst was mixed with an aqueous solution of ruthenium chloride an amount of which was adjusted so that a Ru/Cr ratio was 4.7% by mole and dried in the air at 110° C. for 12 hours. Thereafter, the catalyst was sintered and HF-treated in the same manner as in the preparation of the standard catalyst, and the fluorination was carried out under the above common conditions. The results are as follows:

Activity: 12.2%

Catalyst life: 105 hours

Throughput: 235 g

In comparison with Comparative Example 1, the catalyst life and the throughput were increased without decreasing the activity.

EXAMPLE 2

The chromium hydroxide state catalyst was mixed with an aqueous solution of ruthenium chloride an amount of which was adjusted so that a Ru/Cr ratio was 0.87% by mole and dried in the air at 110° C. for 12 hours. Thereafter, the catalyst was sintered and HP-treated in the same manner as in the preparation of the standard catalyst, and the fluorination was carried out under the above common conditions. The results are as follows:

Activity: 12.3%

Catalyst life: 155 hours

Throughput: 329 g

In comparison with Comparative Example 1, the catalyst life and the throughput were increased without decreasing the activity.

EXAMPLE 3

The chromium hydroxide state catalyst was mixed with an aqueous solution of ruthenium chloride an amount of which was adjusted so that a Ru/Cr ratio was 0.094% by mole and dried in the air at 110° C. for 12 hours. Thereafter, the catalyst was sintered and HF-treated in the same manner as in the preparation of the standard catalyst, and the fluorination was carried out under the above common conditions. The results are as follows:

Activity: 12.1%

Catalyst life: 115 hours

Throughput: 244 g

In comparison with Comparative Example 1, the catalyst life and the throughput were increased without decreasing the activity.

EXAMPLE 4

The chromium hydroxide state catalyst was mixed with an aqueous solution of chloroplatinic acid an amount of which was adjusted so that a Pt/Cr ratio was 0.24% by mole and water was removed with an evaporator followed by the HF treatment in the same manner as in the preparation of the standard catalyst. Using this catalyst, the fluorination was carried out under the above common conditions. The results are as follows:

Activity: 13%

Catalyst life: 63 hours

Throughput: 153 g

In comparison with Comparative Example 2, the catalyst life and the throughput were increased without decreasing the activity.

COMPARATIVE EXAMPLE 2

Using the same standard catalyst as in Example 4, the fluorination was carried out under the common conditions. The results are as follows:

Activity: 13% catalyst life: 40 hours throughput: 93 g

What is claimed is:

1. A process for fluorinating a halogenated hydrocarbon consisting essentially of reacting a halogenated hydrocarbon with hydrogen fluoride in the presence of a fluorination catalyst which comprises a partially fluorinated chromium oxide containing from 0.01–10% by mole, based on the amount of chromium oxide, of at least one metal selected from the group consisting of ruthenium and platinum.

2. The process according to claim 1, wherein said halogenated hydrocarbon is 1,1,1-trifluorochloroethane and 1,1,1,2-tetrafluoroethane is prepared.

3. The process according to claim 1, wherein said chromium oxide is supported on a carrier selected from the group consisting of aluminum oxide, partially fluorinated aluminum oxide and aluminum fluoride.

4. The process according to claim 2, wherein a molar ratio of hydrogen fluoride to said halogenated hydrocarbon is from 0.9:1 to 16:1.

5. The process according to claim 2, wherein a reaction temperature is from 290° C. to 380° C.

6. The process according to claim 1, wherein said catalyst contains 0.01 to 6% by mole of said at least one metal based on an amount of chromium oxide.

7. The process according to claim 1, wherein a molar ratio of hydrogen fluoride to said halogenated hydrocarbon is from 1:1 to 10:1.

8. A process for producing 1,1,1,2-tetrafluoroethane comprising reacting 1,1,1-trifluorochloroethane with hydrogen fluoride in the presence of a fluorination catalyst comprising a partially fluorinated chromium oxide which has either impregnated therein or precipitated thereon from 0.01–10% by mole at least one metal selected from the group consisting of ruthenium and platinum and wherein the molar ratio of hydrogen fluoride to 1,1,1-trifluorochloroethane is from 0.9:1 to 16:1 and said reaction is conducted at a temperature from 290° C. to 380° C.

9. A process for fluorinating a halogenated hydrocarbon consisting of reacting a halogenated hydrocarbon with hydrogen fluoride in the presence of a fluorination catalyst which comprises a partially fluorinated chromium oxide containing from 0.01–10% by mole, based on the amount of chromium oxide, of at least one metal selected from the group consisting of ruthenium and platinum.

* * * * *